United States Patent [19]

Gillet et al.

[11] 4,338,330
[45] Jul. 6, 1982

[54] BENZIMIDAZOLE DERIVATIVES, THEIR USE, AND COMPOSITIONS CONTAINING THESE DERIVATIVES

[75] Inventors: Claude L. Gillet, Blanmont; Joseph L. Roba, Dion-Le-Val; Michel Snyers, Brussels; William R. Van Dorsser, Brussels; Georges E. Lambelin, Brussels, all of Belgium

[73] Assignee: Continental Pharma, Brussels, Belgium

[21] Appl. No.: 145,144

[22] Filed: Apr. 30, 1980

[30] Foreign Application Priority Data

May 4, 1979 [LU] Luxembourg ............ 81225

[51] Int. Cl.$^3$ ............... A61K 31/415; C07D 235/18; C07D 405/12
[52] U.S. Cl. ............... 424/273 B; 548/334; 548/327
[58] Field of Search ............... 548/334, 327; 424/273 B

[56] References Cited

U.S. PATENT DOCUMENTS

| | | | |
|---|---|---|---|
| 3,574,218 | 4/1971 | Hideg et al. | 548/334 |
| 4,130,413 | 12/1978 | Handte et al. | 548/327 |
| 4,212,877 | 7/1980 | Keppe et al. | 424/273 B |

FOREIGN PATENT DOCUMENTS

| | | |
|---|---|---|
| 2737630 | 3/1979 | Fed. Rep. of Germany . |
| 2801953 | 7/1979 | Fed. Rep. of Germany . |
| 2801980 | 7/1979 | Fed. Rep. of Germany . |
| 2905876 | 8/1980 | Fed. Rep. of Germany . |
| 2905877 | 8/1980 | Fed. Rep. of Germany . |
| 1570892 | 5/1969 | France . |
| 1549945 | 8/1979 | United Kingdom . |
| 2014146 | 8/1979 | United Kingdom . |
| 698530 | 11/1979 | U.S.S.R. . |

OTHER PUBLICATIONS

Rote Liste 1977/78, No. 26001-26025.
Crowther et al., J. Med. Chem., 1972, vol. 15(3), pp. 260-266.
Augstein et al., J. Med. Chem. 1973, vol. 16(11), pp. 1245-1251.
Bartsch et al., Drug Research 1977, vol. 27(5), pp. 1022-1026.
Crooks et al., J. Med. Chem. 1979, vol. 22(2), pp. 210-214.
Ullmann's Encyclopädie der Technischen Chemie, 4th Ed., vol. 12, 1976, Verlag Chemie, pp. 636–639.
Hackh's Chemical Dictionary, 4th Ed., pp. 288, 304 and 305, McGraw-Hill, New York, 1969.

Primary Examiner—Henry R. Jiles
Assistant Examiner—N. Harkaway
Attorney, Agent, or Firm—Cushman, Darby & Cushman

[57] ABSTRACT

A derivative of benzimidazole of the general formula I:

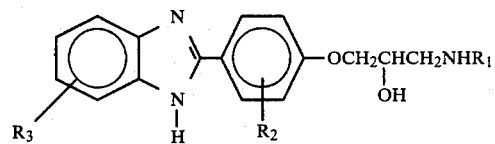

wherein:
$R_1$ represents a linear or ramified alkyl radical $C_1, C_2, C_3, C_4, C_5, C_6, C_7, C_8, C_9, C_{10}, C_{11}, C_{12}, C_{13}, C_{14}, C_{15}, C_{16}, C_{17}$ or $C_{18}$, a cycloalkyl radical $C_3, C_4, C_5, C_6, C_7$ or $C_8$, a linear or ramified alkyl radical $C_1, C_2, C_3, C_4$ or $C_5$ substituted by one or more radicals selected from the group comprising:
phenyl, phenoxy, phenylthio, phenylsufinyl radicals;
phenyl, phenoxy, phenylthio, phenylsulfinyl radicals substituted by one or more linear or ramified alkyl radicals $C_1, C_2, C_3$ or $C_4$, by one or more linear or ramified alkoxy radicals $C_1, C_2, C_3$ or $C_4$, by a methylenedioxy radical, for one or more halogen atoms, such as fluorine, chlorine or bromine;
linear or ramified alkylcarboxamido groups $C_1, C_2, C_3, C_4, C_5$ or $C_6$ optionally substituted by a phenyl or phenoxy radical;
cycloalkylcarboxamido groups $C_1, C_4, C_5, C_6, C_7$ or $C_8$, $R_2$ represents hydrogen, one or more linear or ramified alkyl radicals $C_1, C_2, C_3$ or $C_4$, one or more linear or ramified alkoxy radicals $C_1, C_2, C_3$ or $C_4$, one or more halogen atoms, such as fluorine, chlorine and bromine, $R_3$ represents hydrogen, one or more linear or ramified alkyl radicals $C_1, C_2, C_3$ or $C_4$, one or more linear or ramified alkoxy radicals $C_1, C_2, C_3$ or $C_4$, one or more halogen atoms such as fluorine, chlorine and bromine, one or more nitro groups, as well as esters and salts of such derivatives with non toxic and pharmaceutically acceptable acids.

13 Claims, No Drawings

BENZIMIDAZOLE DERIVATIVES, THEIR USE, AND COMPOSITIONS CONTAINING THESE DERIVATIVES

The present invention relates to benzimidazole derivatives and to esters and salts of these compounds, their processes of preparation, pharmaceutical compositions containing at least one of these derivatives as well as their method of use.

Derivatives according to the invention have the general formula I:

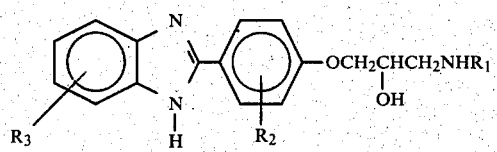

wherein:

$R_1$ represents a linear or ramified alkyl radical $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$ or $C_{18}$, a cycloalkyl radical $C_3$, $C_4$, $C_5$, $C_6$, $C_7$ or $C_8$, a linear or ramified alkyl radical $C_1$, $C_2$, $C_3$, $C_4$ or $C_5$ substituted by one or more radicals selected from the group comprising:
phenyl, phenoxy, phenylthio, phenylsulfinyl radicals;
phenyl, phenoxy, phenylthio, phenylsulfinyl radicals substituted by one or more linear or ramified alkyl radicals $C_1$, $C_2$, $C_3$ or $C_4$, by one or more linear or ramified alkoxy radicals $C_1$, $C_2$, $C_3$ or $C_4$, by a methylenedioxy radical, for one or more halogen atoms, such as fluorine, chlorine or bromine,
linear or ramified alkylcarboxamido groups $C_1$, $C_2$, $C_3$, $C_4$, $C_5$ or $C_6$ optionally substituted by a phenyl or phenoxy radical,
cycloalkylcarboxamido groups $C_3$, $C_4$, $C_5$, $C_6$, $C_7$ or $C_8$.

$R_2$ represents hydrogen, one or more linear or ramified alkyl radicals $C_1$, $C_2$, $C_3$ or $C_4$, one or more linear or ramified alkoxy radicals $C_1$, $C_2$, $C_3$ or $C_4$, one or more halogen atoms, such as fluorine, chlorine and bromine, $R_3$ represents hydrogen one or more linear or ramified alkyl radicals $C_1$, $C_2$, $C_3$ or $C_4$, one or more linear or ramified alkoxy radicals $C_1$, $C_2$, $C_3$ or $C_4$, one or more halogen atoms, such as fluorine, chlorine and bromine, one or more nitro groups.

According to a preferred embodiment of the invention, the latter relates to compounds of formula I wherein:

$R_1$ represents a linear or ramified alkyl radical $C_3$–$C_{12}$, preferably a $C_3$–$C_8$ alkyl, a cycloalkyl $C_5$–$C_6$ radical, a linear or ramified alkyl $C_2$–$C_5$, preferably a $C_2$–$C_4$ alkyl substituted by one or more radicals selected from the group comprising:
phenyl, phenoxy, phenylthio, phenylsulfinyl radicals,
phenyl, phenoxy, phenylthio, phenylsulfinyl radicals substituted by one or two methyl radicals, by one or two methoxy radicals, by a methylenedioxy radical, by one or two halogen atoms, such as fluorine and chlorine,
linear or ramified alkylcarboxamido $C_1$–$C_4$ groups optionally substituted by a phenyl or phenoxy group,
cycloalkylcarboxamido $C_5$–$C_6$ groups, $R_2$ represents hydrogen, at least one $C_1$–$C_4$ straight or branched alkyl, preferably one or two methyl radicals, at least one $C_1$–$C_4$ straight or branched alkoxy, preferably one or two methoxy radicals, one or two halogen atoms, such as fluorine or chlorine, $R_3$ represents hydrogen, at least one $C_1$–$C_4$ straight or branched alkyl, preferably one or two methyl radicals, at least one $C_1$–$C_4$ straight or branched alkoxy, preferably one or two methoxy radicals, one or two halogen atoms such as fluorine, chlorine or bromine, one or two nitro groups.

A preferred class of compounds of formula I is that wherein $R_1$ represents a linear or ramified alkyl $C_3$–$C_8$ radical, a linear or ramified alkyl $C_2$–$C_4$ radical substituted by a radical selected from the groups comprising:
phenyl, phenoxy, phenylthio radicals,
phenyl, phenoxy, phenylthio radicals substituted by one or two methyl radicals, by one or two methoxy radicals, by a methylenedioxy radical, $R_2$ represents hydrogen, one or two methyl radicals, one or two methoxy radicals, $R_3$ represents hydrogen, a methyl radical, a methoxy radical, a nitro group $R_1$ may also be a linear or branched $C_6$–$C_{10}$, preferably $C_3$–$C_4$ alkyl group, optionally substituted, or one of isopropyl, t-butyl, 2-phenoxyethyl, (1-methyl-3-phenyl)propyl, (1-methyl-4-phenyl) butyl, 4-phenylbutyl or 2-(3,4-dimethoxyphenyl)ethyl.

A particular class of products according to the invention is comprised of products of formula I wherein:

$R_1$ represents a linear or ramified alkyl $C_6$–$C_{10}$ radical
$R_2$ and $R_3$ represent hydrogen.

Are particularly preferred, the products of formula I wherein:

$R_1$ represents a linear or ramified alkyl $C_3$–$C_4$ radical, a linear or ramified alkyl $C_2$–$C_4$ radical substituted by a radical selected from the group comprising:
phenyl and phenoxy radicals,
phenyl and phenoxy radicals substituted by one or two methyl radicals, by one or two methoxy radicals, $R_2$ and $R_3$ represent hydrogen.

Are more particularly interesting, the products of formula I wherein:

$R_1$ represents an isopropyl, t-butyl, 2-phenoxyethyl, (1-methyl-3-phenyl)propyl, (1-methyl-4-phenyl)butyl, 4-phenylbutyl, 2-(3,4-dimethoxyphenyl)ethyl radical, $R_2$ and $R_3$ represent hydrogen.

Examples of compounds according to the invention are:

2-[4-(3-isopropylamino-2-hydroxypropoxy)phenyl]benzimidazole

2-{4-[3(2-phenoxyethylamino)-2-hydroxypropoxy]phenyl}benzimidazole

2-{4-[3-[2-(3,4-dimethoxyphenylethyl)amino]-2-hydroxypropoxy]phenyl}benzimidazole 2-[4-(3-t-butylamino-2-hydroxypropoxy)phenyl]benzimidazole.

2-[4-(3-n-octylamino-2-hydroxypropoxy)phenyl]benzimisazole.

2-[4-(3-n-octadecylamino-2-hydroxypropoxy)phenyl]benzimidazole.

2-{4-[3-(2-octylamino)-2-hydroxypropoxy]phenyl)}benzimidazole.

2-{4-[3-(2-phenylacetamidoethyl)amino-2-hydroxypropoxy]phenyl}benzimidazole.

2-{4-[3-(2-isobutyramidoethyl)amino-2-hydroxy-propoxy]phenyl}benzimidazole.

2-{4-[3-(2-cyclopentylamidoethyl)amino-2-hydroxy-propoxy}phenyl}benzimidazole.

2-[4-(3-isopropylamino-2-hydroxypropoxy)-3-bromophenyl]benzimidazole.

2-[4-(3-isopropylamino-2-hydroxypropoxy)-3-methoxyphenyl]benzimidazole.

2-[4-(3-isopropylamino-2-hydroxypropoxy)-2,6-dimethylphenyl]benzimidazole.

2-[4-(3-isopropylamino-2-hydroxypropoxy)-phenyl]-5(6)nitrobenzimidazole.

Suitable esters of oxypropanolamines according to the invention are for example esters deriving from aliphatic carboxylic acids comprising up to 20 carbon atoms, such as acetic, palmitic, stearic or oleic acid, and esters deriving from aromatic carboxylic acids comprising up to 10 carbon atoms, such as benzoic acid, as well as their addition salts with acids.

If derivatives according to Formula I are as addition salts with acids, they can be transformed according to usual processes into their free base or into salts with other acids.

The most currently used salts are addition salts with acids, in particular addition salts with non toxic, pharmaceutically usable acids comprised of suitable inorganic acids, for example hydrochloric, sulfuric or phosphoric acid or of suitable organic acids, such as aliphatic, cycloaliphatic, aromatic, araliphatic or heterocyclic, carboxylic or sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, hydroxybenzoic, salicylic, phenylacetic, mandelic, embonic, methanesulfonic, ethanesulfonic, panthotenic, toluenesulfonic, sulfanilic, cyclohexylaminosulfonic, stearic, alginic, $\beta$-hydroxypropionic, $\beta$-hydroxybutyric, oxalic, malonic, galactaric, galacturonic acids. These salts can also derive from natural or not amino acids, such as lysine, glycine, arginine, ornithine, asparagine, glutamine, alanine, valine, threonine, serine, leucine, cysteine and the like.

The compounds of formula I comprise at least one asymmetrical carbon atom and thus exist as optical isomers or racemics; all these forms form a part of the invention.

The optical isomers can be obtained by resolution of racemics according to traditional processes, for example by formation of diastereoisomers salts by action of optically active acids, such as tartaric, diacetyltartaric, tartranilic, dibenzoyltartaric, ditoluoyltartaric, and separation of the diastereoisomer mixture for example by crystallization or chromatography, then liberation of the optically active bases from these salts. The optically active compounds of formula I may also be obtained by using optically active starting products. The preferred optical isomers of the compounds of formula I are those having the (S) configuration at the level of the carbon atoms bearing the alcohol function in the oxypropanolamine chain.

In general, the derivatives according to the invention have some activities on the cardiovascular system, for example activities inhibiting platelet agglutination, antihypertensive, $\beta$-blocking, locally anesthesic, antispasmodic, peripheral vasodilator, hypolipidemic, antithrombotic, antiarrhythmic activities and/or activities on the central nervous system, for example a tranquillizing activity.

These properties allow to contemplate use of the products of the invention in the prophylaxis and the treatment of hypertension and of cardiovascular affections, such as atherosclerosis and anginapectoris, myocardial infarction and rythm disturbances.

More particularly, it has been found that some products according to the invention have an important effect of selective blocking of $\beta_1$ adrenergic receptors and are thus beta-adrenergic blocking agents. The compounds having this selective effect have a higher specificity for cardiac $\beta$-adrenergic receptors ($\beta_1$) than for $\beta$-adrenergic receptors of peripherical blood vessels and of bronchial muscles ($\beta_2$).

This cardioselectivity allows to contemplate use of the products of the invention for patients induring asthma and chronic pulmonal disturbances, as well as those suffering from peripheral arterial insufficiencies. Moreover, the products of the invention do not present neither any $\beta$-mimetic activity (partial antogonists), nor membrane effects, as it may be concluded from the absence of modifications in the frequency of auricle contraction in any direction.

It has also been observed that some of the products of the invention have an important antihypertensive activity which is rapid and of long duration of action; this distinguishes said particular compounds from $\beta$-blocking agents presently used in therapeutics in the treatment of hypertension.

It has also been observed that the products according to the invention were endowed at the same time with an important blocking activity of the $\beta_1$ adrenergic receptors and with an important peripheral vasodilator activity.

It is known presently that peripheral vasodilator agents have an increasing interest in the treatment of hypertension. It is however appeared that said agents have undesirable side effects, such as for example tachycardia, which is necessary to decrease by simultaneous administration of a $\beta$-blocking agent. A molecule having at the same time $\beta_1$-blocking properties and peripheral vasodilator properties has thus a real therapeutical interest.

The present invention also claims pharmaceutical compositions comprising as active ingredient, at least one compound of general formula I and/or one of its salts or one of its esters with a pharmaceutical excipient. These compositions are prepared in order that they can be administered orally, rectally or parenterally.

Thus for example compositions for oral administration can be liquids or solids and be prepared as tablets, capsules, granules, powders, syrups or suspensions; such compositions comprise additives and excipients generally used in galenic pharmacy, inert diluents, desintegration agents, binders and lubricants, such as lactose, starch, talc, gelatin, stearic acid, silicic acid, magnesium stearate, polyvinyl pyrrolidone, calcium phosphate, calcium carbonate and the like.

Such formulations can be prepared in order to delay desintegration and consequently the activity duration of the active component.

The aqueous suspensions, the emulsions and the oily solutions are prepared in the presence of sweetening agents, such as dextrose or glycerol, perfuming agents such as vanillin for example, and may also contain thickening agents, wetting agents, preservation agents.

The oily emulsions and solutions are made in an oil of vegetal or animal origin and may contain emulsifying, perfuming, dispersing, sweetening and antioxydant agents. For parenteral administration, sterile water, an aqueous solution of polyvinylpyrrolidone, peanut oil, ethyl oleate and the like are used as vehicle. These aqueous or oily injectable solutions may contain thickening, wetting, dispersing and gelling agents.

The compounds according to the invention are prepared by the following processes which form a part of this invention and are defined hereinafter.

In the case of these processes giving rise to the production of new intermediate compounds, these new compounds and also the processes used for their preparation also form a part of this invention.

The synthesis of the oxypropanolamine chain may be made at any stage of the elaboration of the benzimidazole nucleus, and also the formation of the benzimidazole nucleus may be made at any stage of the synthesis of the oxypropanolamine.

A. Synthesis of the oxypropanolamine chain.

The phenoxypropanolamine derivatives and their salts are advantageously prepared from a compound of formula II:

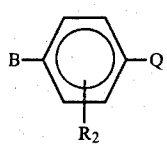

II or optionally according to the meaning of Q from a salt of a compound having this formula where Q represents one of the following groups:

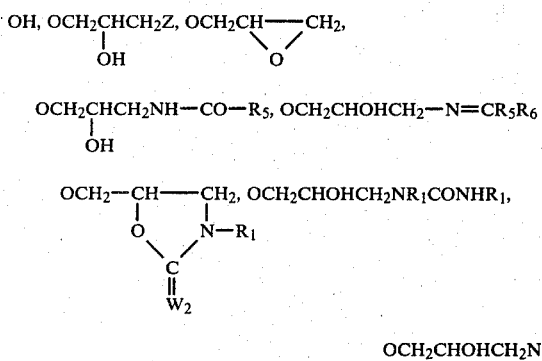

$OCH_2CHOHCH_2NH_2$ $R_1$ is such as hereinabove defined, Z is a halogen atom such as chlorine, bromine or iodine, an amino $NH_2$ group or a group which can easily give rise to a substitution reaction such as for example a group $OSO_2R_9$, $R_9$ is an alkyl $C_1-C_4$ radical or an aliphatic nucleus or an aromatic nucleus such as phenyl or tolyl so that groups such as tosyl or mesyl are formed, $R_5$ is such that $R_5CH_2$ represents the radical $R_1$, $R_6$ is an alkyl $C_1-C_4$ radical such that radical $R_5-CHR_6$ is compatible with the meanings given for $R_1$, $C=W_2$ represents a carbonyl or methylene group so that the heterocycle is an oxazolidone or an oxazolidine, B represents the benzimidazole nucleus optionally substituted by the radical $R_3$ such as defined for the general formula or this benzimidazole nucleus at any stage of elaboration, such as described in paragraph B.

This fundamental general method comprises several variants which are described hereinafter.

A. 1. According to this first variant, a phenol derivative III is alkylated according to the scheme:

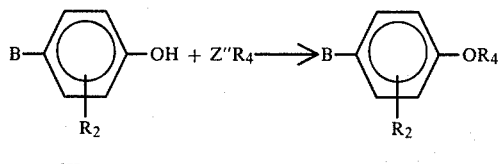

III

Z″ represents a halogen atom, such as chlorine, bromine, iodine or a group able to give rise to a substitution reaction with an amine, such as tosyl or mesyl groups, $R_2$ and B have been previously defined, $R_4$ represents the groups:

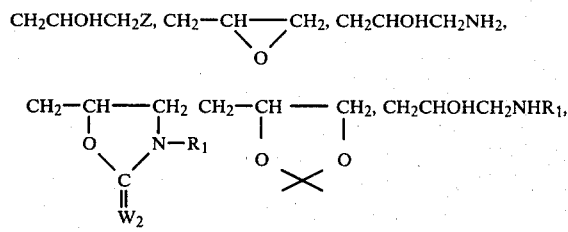

wherein $R_1$, Z and $W_2$ have the hereinabove given meanings.

In this process, the reaction may be made preferably by using a basic compound as dehydrohalogenating agent, in a suitable solvent at a temperature between room temperature and 200° C. As examples of suitable solvent, may be mentioned a lower alcohol, such as methanol, ethanol or isopropanol, a ketone, such as acetone, an ether such as dioxan, diethyl or dimethyl ether of diethylene glycol an aromatic or aliphatic hydrocarbon, such as benzene, toluene or petroleum ether. As examples of basic compounds, may be cited sodium hydroxide, potassium hydroxide, sodium carbonate, potassium carbonate, sodium methoxide, sodium hydride, sodium amide, potassium t-butoxide, pyridine, N-dimethylaniline and triethylamine.

A. 2. According to this variant, an amine IV is alkylated so as to form the product V:

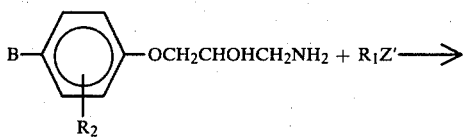

IV

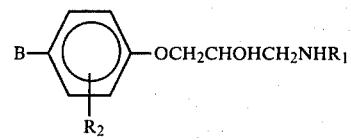

V $R_1$, $R_2$ and B have been previously defined. $Z_i$ is $NH_2$ The reaction advantageously develops in an inert organic solvent, such as chlorinated hydrocarbons, for example chloroform or dichloromethane, aromatic or aliphatic hydrocarbons, such as benzene, toluene or also acetonitrile and ethers. The temperature is comprised between room temperature and the reflux temperature of the reaction mixture. The reaction may be advantageously made in the presence of an organic base, such as pyridine, triethylamine or N-dimethylaniline or of an inorganic base, such as hydroxides, carbonates and bicarbonates of alkaline or alkaline-earth metals or of finely ground lime.

A variant of this process is hereinafter illustrated.

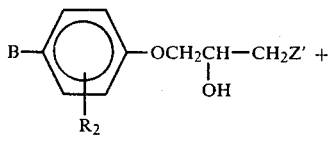

VI

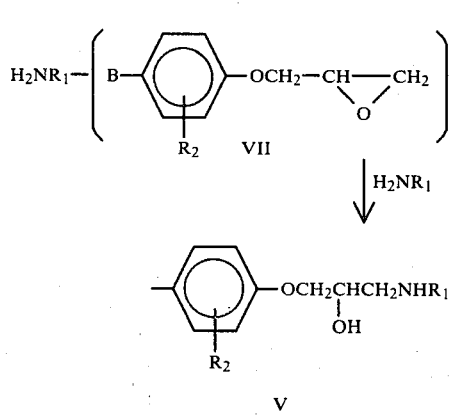

$R_1$, $R_2$, B and Z′ have been previously defined.

It will be seen that this reaction and the preceding one are two alkylation reactions of a primary amine into a secondary amine. It is obvious that the operation conditions for both said reactions are quite comparable. It is to be noted that it is sometimes interesting to form oxirane VII quantitatively by treating the compound VI with a basic agent, such as hydroxides of alkaline or alkalineearth metals or alkoxides of alkali metals, then to react this oxirane with an amine as hereinabove described. This variant forms the subject of paragraph A6.

A. 3. According to this process, a primary amine is subjected to an acylation followed by a reduction in order to form the compound V according to the scheme:

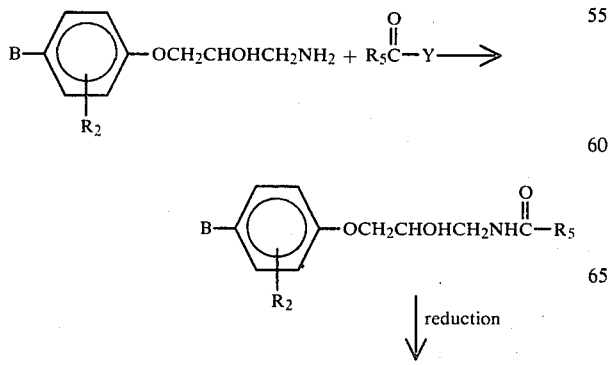

-continued

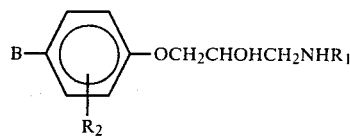

V $R_1$, $R_2$ and B have been previously defined, $R_5$ is such that $R_5CH_2$ represents the radical $R_1$ and Y represents a halogen such as chlorine or bromine or a good leaving group such as tosyl, mesyl or acyloxy groups.

The reaction is advantageously developed in an inert organic solvent, such as chlorinated hydrocarbons, for example chloroform or dichloromethane, aromatic or aliphatic hydrocarbons, such as benzene, toluene or petroleum ether, alcohols such as methanol and ethanol or also acetonitrile and ethers. The temperature is comprised between room temperature and the reflux temperature of the reaction mixture. The reaction may advantageously be made in the presence of an organic base, such as pyridine, triethylamine or N-dimethylaniline or of an inorganic base, such as hydroxides, carbonates and bicarbonates of alkaline or alkaline-earth metals and of finely ground lime. The reaction is completed by reduction of amide in amine. Many processes have been described for carrying out such a reduction; it may be mentioned, for example, hydrogenation in the presence of Raney nickel or cupric chromite in inert solvents such as lower alcohols, for example methanol or ethanol or also acetic acid, reduction by lithium aluminium hydride in ethers such as diethyl ether, dioxan or tetrahydrofuran.

If in the hereinbefore described process Y represents hydrogen or an alkyl radical, the intermediate as formed is then an imine VIII which leads to compound V by reduction.

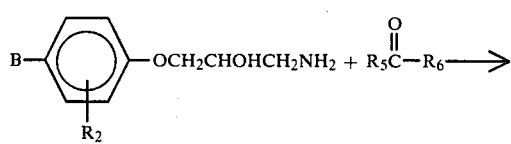

IV

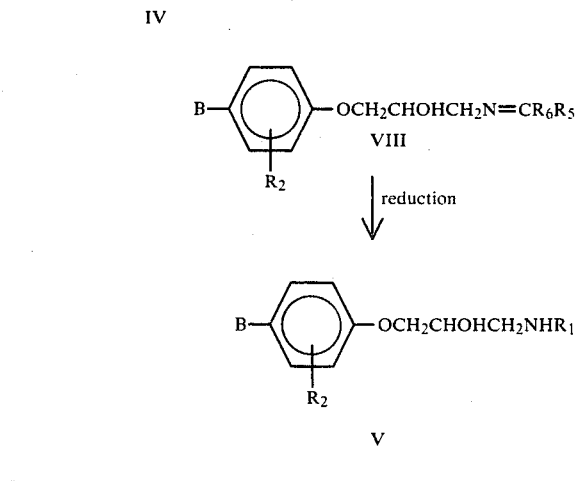

V $R_1$, $R_2$, $R_5$ and B have been previously described. $R_5$ represents an alkyl $C_1$–$C_4$ radical so that the radical

is compatible with the meanings given for $R_1$.

The condensation reaction is made in an inert organic solvent, preferably water immiscible, such as for example aromatic hydrocarbons, for example benzene, toluene or petroleum ether, chlorinated solvents such as carbon tetrachloride or chloroform or ethers. The reaction advantageously develops at a higher temperature than room temperature. An acid catalyst such as hydrochloric acid, sulfuric acid and p-toluenesulfonic acid is traditionally added to the reaction mixture.

The reduction is made in the presence of hydrogen and of a hydrogenation catalyst, such as platinum, platinum oxide or palladium on carbon in a solvent such as methanol, ethanol, ethyl acetate in glacial acetic acid at ordinary pressure and more advantageously at a higher pressure, or with an alkaline metal hydride, such as sodium borohydride in a solvent such as methanol or aluminium lithium hydride in a solvent such as ether or tetrahydrofuran.

A. 4. By means of this new process, an oxazolidone IX or an oxazolidine X is hydrolysed into propanolamine according to the scheme:

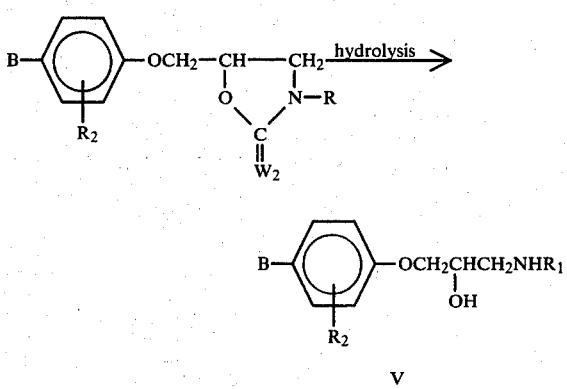

IX: $C=W_2$ represents $C=O$
X: $C=W_2$ represents $CH_2$.

The hydrolysis of these heterocyclic compounds is traditionally made in an aqueous acid medium. The acid may be mineral, such as for example hydrochloric, sulfuric, phosphoric acid, or organic such as for example acetic acid. In some cases, it may be advantageous, in order to accelerate the reaction, to bring the temperature of the reaction mixture from room temperature to reflux temperature.

A. 5. According to this way of proceeding, the oxypropanolamine chain is elaborated from an acetal or from a cetal of a glycol XI according to the scheme:

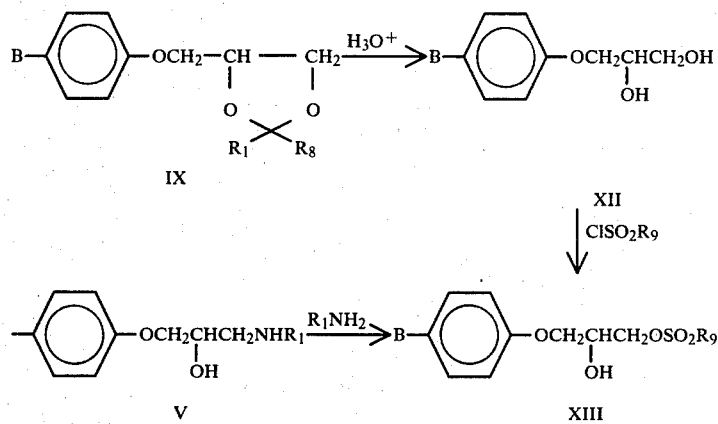

$R_1$, $R_2$ and B have been previously defined, $R_7$ and $R_8$ which may be identical or different represent hydrogen or a linear or ramified alkyl $C_1$–$C_4$ radical and $R_9$ represents a linear or ramified alkyl $C_1$–$C_4$ radical or an aromatic nucleus, such as a phenyl radical or a tosyl radical.

The compound XI is hydrolysed in an aqueous acid medium. The acid may be selected from inorganic acids, such as hydrochloric acid, sulfuric acid, phosphoric acid or from organic acids such as acetic acid or propionic acid. It may be advantageous to slightly heat the reaction mixture to carry out or complete the reaction. The diol XII so obtained is treated with a sulfonic acid chloride so as to transform the primary hydroxyl radical into a good leaving group. This reaction is made in an inert organic solvent, such as chlorinated hydrocarbons, for example chloroform or dichloromethane or such as aromatic or aliphatic hydrocarbons, for example benzene, toluene or petroleum ether or such as ethers for example diethyl ether, dioxan or tetrahydrofuran. The reaction of the compound XIII with the amine is an alkylation reaction described in the process A.2.

It is finally to be noted that this process allows to selectively obtain phenylethylamines of R or S configuration from optically active glycols. A.6. A preferred process of the invention consists of using a phenol XIV, epichlorhydrin XV and an amine $R_3NH_2$ according to the scheme:

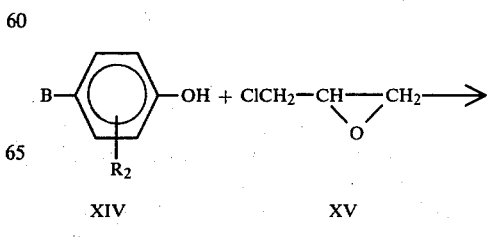

-continued

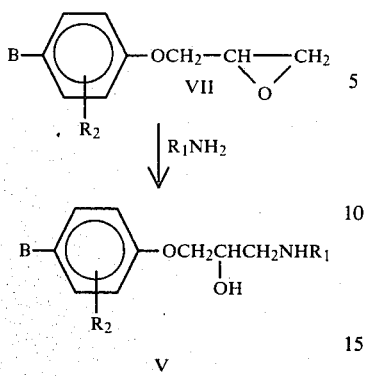

$R_1$, $R_2$ and B have been previously defined. The first step of the process is made in an inert organic solvent, such as aromatic or aliphatic hydrocarbons, for example benzene, toluene, petroleum ether or chlorinated hydrocarbons, such as chlorobenzene, chloroform or dichloromethane. Are generally preferred slightly polar solvents such as for example acetone, methyl ethyl cetone or methyl isobutyl cetone. It may also be advantageous to use a mixture of known solvents, for example the dioxan-ethanol-water mixture. The reaction develops at a temperature comprised between room temperature and reflux temperature. The presence of a base helps to the good development of the reaction. This base may be an alkaline metal carbonate, such as potassium or sodium carbonate or an organic base.

The transformation of the epoxide VII in propanolamine V under the action of the amine is carried out in an inert organic solvent such as alcohols for example methanol, ethanol, propanol, butanol or such as aromatic or aliphatic hydrocarbons, chlorinated or not, such as benzene, toluene, petroleum ether, chloroform, or such as cetones for example acetone or methyl ethyl cetone. This reaction may also be made without solvent, in the presence of excess amine. It develops at a temperature comprised between 0° C. and reflux temperature.

A. 7. According to this way of proceeding, an azetidinol XVI is reacted with a phenol derivative XIV so as to form the oxypropanolamine V.

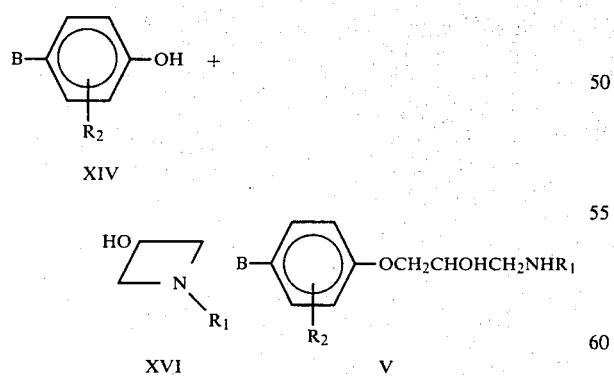

$R_1$, $R_2$ and B have been previously defined. This reaction develops in the presence of water. An inert organic cosolvent may also be used. Advantageously the reaction mixture will be basic. Traditionally the base used is an alkaline metal hydroxide, such as sodium or potassium hydroxide. The temperature at which the reaction is carried out is comprised between 130° and 250° C., preferably about 150° C.

A. 8. According to this process, an urea of formula XVII is thermolysed:

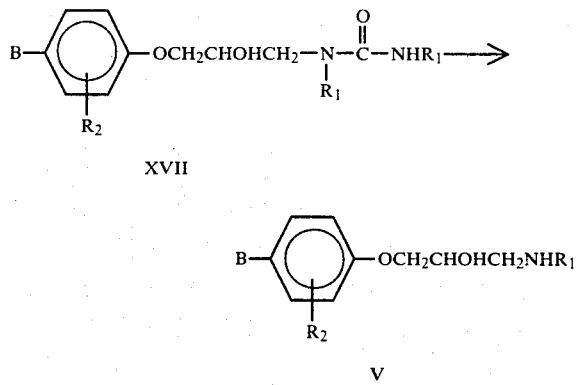

$R_1$, $R_2$ and B have been previously defined. The thermolysis reaction is led either without solvent (in pure phase), or in inert organic solvents of very high boiling point, such as tetraline, decaline or ligroin. The reaction may be made under normal pressure or under vacuum. The thermolysis of urea develops at temperatures of about 200° C.

B. Synthesis of the benzimidazole nucleus.

Several classical processes forming the benzimidazole nucleus are mentioned hereinafter.

Generally, the benzimidazole nucleus may be synthetized at any stage of the synthesis of the oxypropanolamine chain by taking care however to suitably protect the functions sensible to conditions and reactants used in the synthesis of the benzimidazole nucleus.

B. 1. According to this first way of proceeding, the starting reactant is a benzonitrile derivative XVIII which is transformed into imidate XIX, then cyclised into benzimidazole XX according to the scheme:

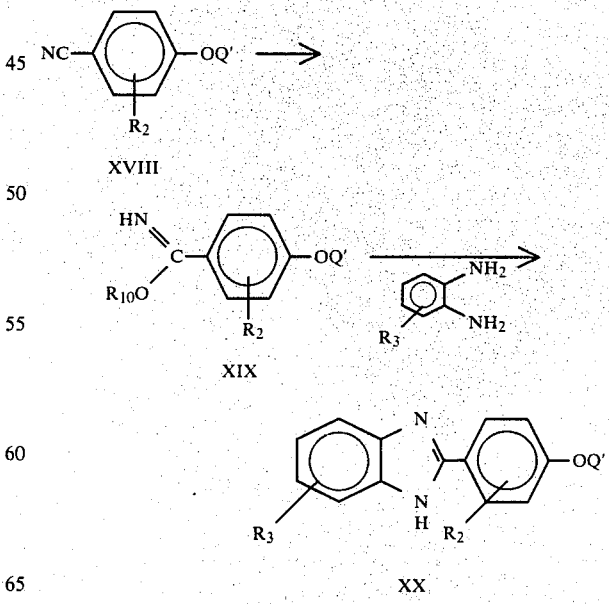

$R_2$ and $R_3$ have been previously defined, Q represents the propanolamine chain, this chain at any stage of its elaboration, hydrogen or a protective group for the phenol function such as a benzyl group, a tetrahydropyranyl group, a tetrahydrofuranyl group, an alkylthiomethyl group, an alkoxymethyl group, an acyl group, a benzoyl group, a linear or ramified alkyl $C_1$–$C_4$ or alkenyl $C_2$–$C_4$ group, a trialkylsilyl group and the like and $R_{10}$ represents a lower alkyl $C_1$–$C_4$ radical.

The compound XVIII and an alcohol $R_{10}OH$ are brought together in acid or basic medium. The acid used is generally an inorganic acid such as hydrochloric acid or sulfuric acid. If the reaction is made in basic medium, the base is usually alkaline metal alkoxide. This reaction develops preferably in an alcohol such as methanol, ethanol, propanol, isopropanol, butanol or t-butanol at a temperature between 0° C. and the reflux temperature of the solvent.

The reaction between the imidate XIX and the o-phenylenediamine derivative is made in an inert organic solvent, such as alcohols for example methanol, ethanol or propanol, chlorinated solvents such as chloroform or dichloromethane or aromatic or aliphatic hydrocarbons, such as benzene, toluene or petroleum ether. The reaction is made at a temperature between 0° C. and the reflux temperature of the reaction mixture.

Variants of this process consist of reacting no longer a nitrile but an aldehyde, a carboxylic acid, an acid halide, an anhydride, an amide or an ester with o-phenylenediamine under the conditions hereabove described.

B. 2. According to this way of proceeding, an amidine of formula XXI is cyclised intramolecularly to form a benzimidazole derivative XX:

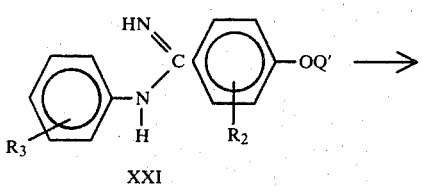

XXI

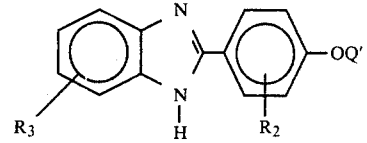

XX $R_2$, $R_3$ and $Q'$ have been previously defined. The reaction is made in an inert organic solvent, such as aromatic or aliphatic hydrocarbons, for example benzene, toluene, xylene, petroleum ether or ligroin or such as chlorinated hydrocarbons for example chloroform, dichloromethane or carbon tetrachloride, or such as alcohols for example methanol or ethanol or such as ethers for example dimethyl ether of diethylene glycol. This reaction develops at a temperature between room temperature and the reflux temperature of the solvent. It may be also advantageous to add a catalyst or a reactant such as sodium hypochlorite so as to obtain better yields of products.

B.3. According to this way of proceeding, a derivative of o-nitroaniline XXII is reacted with an active derivative of a substituted benzoic acid XXIII according to the scheme:

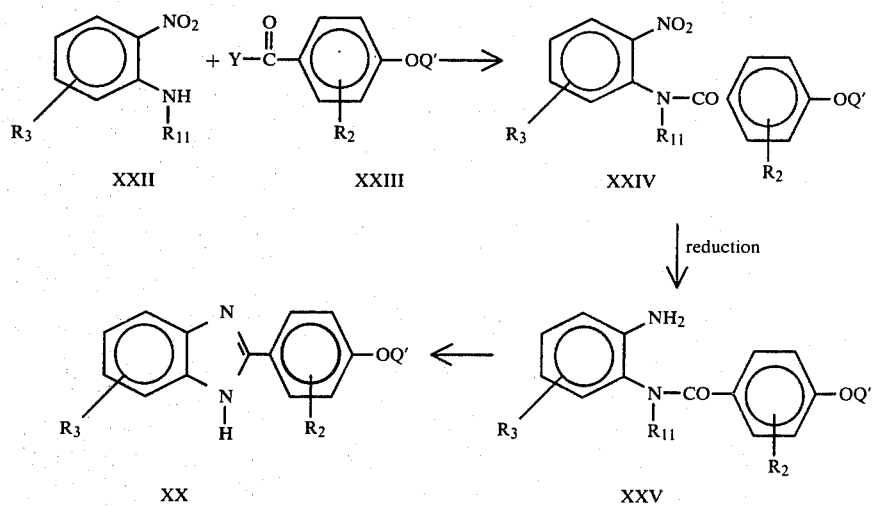

$R_2$, $R_3$ and $Q'$ have been previously defined while Y has been defined as being a halogen such a chlorine or bromine or a good leaving group such as tosyl, mesyl, or acyloxy groups, $R_{11}$ represents hydrogen or a protective group for the amine function such as the benzyl group for example. The reaction between compounds XXII and XXIII is an acylation reaction of an amine. Such a reaction has been described in paragraph A.3. It is obvious that the operation conditions are comparable to those described in this paragraph. The reduction of the nitro group into amine (passage from XXIV to XXV) may be made by using reactants such as hydrogen with catalysts of the class comprising transition metals and their oxides, lithium aluminium hydride, metals such as zinc, tin and iron, and salts such as titanium chloride, stannous chloride, iron sulfate.

The inert organic solvent used to carry out the reduction is selected according to the reducing agent used from alcohols such as methanol or ethanol, acids such as glacial acetic acid, ethers such as diethyl ether, dioxan or tetrahydrofuran.

The reduction is carried out at a temperature between 0° C. and the reflux temperature of the solvent.

The cyclisation of the amine XXV into benzimidazole XX is made in water or in an inert organic solvent such as benzene, toluene, carbon tetrachloride, chloroform. However, solvents such as alcohols for example methanol and ethanol may also be used. This reaction develops at a higher temperature than room temperature and advantageously at the reflux temperature of the reaction mixture. Advantageously, the reaction is catalysed with an acid such as hydrochloric acid, sulfuric acid or p-toluenesulfonic acid.

The deprotection of the amine completes the reaction. This deprotection may however be made in a previous phase. According to the nature of the protective group, the deprotection may be carried out by acid or basic hydrolysis, by oxidation or by reduction.

A variant of this process is obtained when Y represents hydrogen or $R_6$. The product of this reaction with the o-nitrianiline derivative is then a N-benzylidene-2-nitroaniline XXVI the nitro group of which is then reduced into an amine. The cyclisation of the derivative XXVII completes the process.

A variant of the fundamental process and of the previous variant consists of using an o-azidoaniline XXVIII instead of an o-nitroanilin.

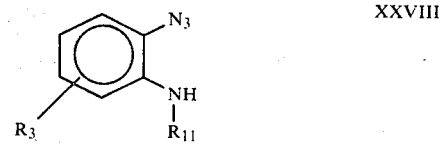

by passing through one of the intermediate products:

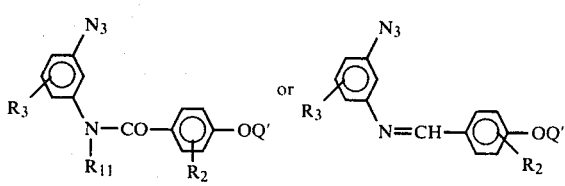

The reaction scheme is identical to the previous one, as well as the operation conditions.

Hereinafter are given detailed examples of preparation of some phenoxypropanolamine derivatives according to the invention. These examples have more particularly for their object to more completely illustrate the particular features of the processes according to the invention.

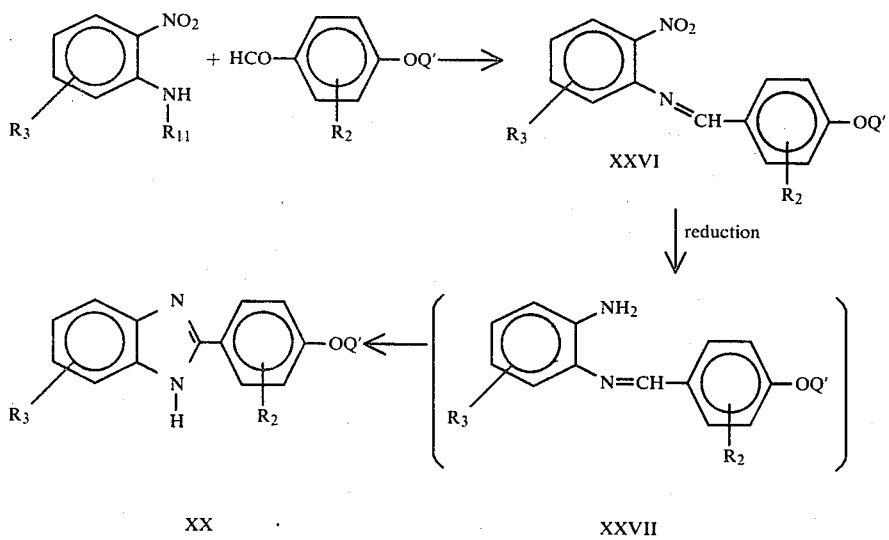

$R_2$, $R_3$, Q and $R_{11}$ have been previously defined. The condensation reaction is carried out in an inert organic solvent, preferably water immiscible, such as for example aromatic hydrocarbons such as benzene, toluene and petroleum ether, chlorinated solvents such as carbon tetrachloride or chloroform or ethers. The reaction advantageously develops at a higher temperature than room temperature. An acid catalyst such as hydrochloric acid, sulfuric acid and p-toluenesulfonic acid is traditionally used in the reaction mixture.

The reduction develops such as in the fundamental process B3 but the amino derivative, depending upon the reaction conditions, is not compulsorily isolated, it may be cyclised in situ by heating the reaction mixture which contains the derivative XXVI and the reducing agent in the solvent selected from the inert organic solvents, such as benzene, toluene, t-butylbenzene, xylene or aliphatic hydrocarbons or high boiling point.

EXAMPLE 1

2-[4-(3-isopropylamino-2-hydroxypropoxy)phenyl]-benzimidazole.

(a) A solution of 30 g (128 mmols) of 1-p-cyanophenoxy-3-isopropylamino-2-propanol in 200 ml of absolute ethanol was saturated with dry gaseous hydrochloric acid. The solution was kept from contact with the air for one night, then diluted with ether. The precipitate was filtered and recrystallized from a mixture of ethanol and ether. Thus 41.6 g (118 mmols) of iminoether were obtained as dihydrochloride.

Yield: 92% MP (°C.): 136–137 (with decomposition).

(b) 21 g (59 mmols) of the preceding product were added at a time to a solution of 6.4 g (59 mmols) of orthophenylenediamine in 80 ml of anhydrous ethanol.

The mixture was stirred for 24 hours at room temperature and under inert atmosphere (nitrogen). The mixture was then evaporated to dryness under reduced pressure and the residue after dilution with 150 ml of water was basified (pH 14) with 10% aqueous soda. The precipitate formed was filtered, washed repeatedly with chloroform, then water and dried. After recrystallization from acetone, 12 g (37 mmols) of the final product were obtained.

Yield: 63% MP (°C.) 193–194.

| Elementary analysis | C | H | N |
| --- | --- | --- | --- |
| % calculated | 70.1 | 7.1 | 12.9 |
| % found | 69.9 | 7.1 | 12.9 |

EXAMPLE 2

2-{4-[3-(2-phenoxyethylamino)-2-hydroxypropoxy]-phenyl}benzimidazole.

(a) 17 g (55 mmols) of 1-p-cyanophenoxy-3-(2-phenoxyethylamino)-2-propanol were suspended in 200 ml of 22% by weight hydrochloric acid.

The mixture was agitated for 18 hours at room temperature, after which a total setting was observed. The mixture was then centrifuged and the white solid obtained was twice recrystallized from ethanol. Weight: 17.3 g (41 mmols; 75%) MP (°C.): 110 (decomposition)

(b) A solution of 4.2 g (39 mmols) of orthophenylenediamine in 50 ml of methanol was added with 16.2 g (39 mmols) of the preceding iminoether hydrochloride which dissolves quickly. The mixture was agitated at room temperature for 1.5 hour, which causes formation of an abundant precipitate. The suspension was then added with 300 ml of a 10% aqueous soda solution, then three times extracted with chloroform. Evaporation of combined organic extracts leaves a red oil which spontaneously crystallizes. After two recrystallizations from a ethanol/ethyl acetate mixture 1/1, the product was white and weighted 8.2 g (20 mmols; 51%) MP (°C.): 152–153.

| Elementary analysis | C | H | N |
| --- | --- | --- | --- |
| % calculated | 71.4 | 6.3 | 10.4 |
| % found | 71.1 | 6.4 | 10.4 |

EXAMPLE 3

2-[[4-{3-[2-(3,4-dimethoxyphenyl)ethylamino]-2-hydroxypropoxy}phenyl]]benzimidazole.

This compound was obtained following the method of operation described in the preceding example, from 1-p-cyanophenoxy-3-[2-(3,4-dimethoxyphenyl)ethylamino]-2-propanol.

MP (°C.): 162.5–163

| Elementary analysis | C | H | N |
| --- | --- | --- | --- |
| % calculated | 69.8 | 6.5 | 9.4 |
| % found | 69.7 | 6.7 | 9.4 |

EXAMPLE 4

2-[4-(3-isopropylamino-2-hydroxypropoxy)-3-methyl)phenyl]benzimidazole.

(a) To a mixture of 6.7 g (44 mmols) of 4-hydroxy-3-methylbenzoic acid, of 6.1 g (44 mmols) of orthonitroaniline and of 75 ml of benzene, 4 ml (6.3 g, 46 mmols) of phosphorous trichloride were added. The mixture was then heated to reflux temperature for 24 hours. The reaction mixture when brought back to room temperature was diluted with 75 ml of 10% hydrochloric acid, then extracted five times with ethyl acetate. The combined extracts were washed with water, then dried on magnesium sulfate before being concentrated till a volume of about 50 ml. Agitation of the residue causes 4-hydroxy-3-methyl-2'-nitrobenzanilide to be precipitated, which is purified by recrystallization from isopropanol.

Yield: 6.8 g (57%); MP (°C.): 208–210.

(b) To 120 ml of acetone, 6.5 g (24 mmols) of the preceding phenol, 2.8 ml (3.3 gr; 36 mmols) of epichlorohydrin and 6.6 g (48 mmols) of potassium carbonate were successively added. The mixture was heated to reflux temperature until thin layer chromatography on silica indicates that the starting phenol has disappeared when made with a benzene/acetone mixture 9/1 as solvent. The mixture when brought back to room temperature was diluted with water, then extracted with ethyl acetate. The organic extract was dried on magnesium sulfate, then evaporated to dryness under reduced pressure. The residue when recrystallized from isopropanol gave the expected 4-(2,3-epoxypropoxy)-3-methyl-2'-nitro-benzanilide.

Yield: 4.0 g (12 mmols; 50%). MP (°C.): 102–104

(c) The preceding product (4.0 g; 12 mmols) was mixed with 40 ml of ethanol. Then 3.1 ml (2.12 g; 36 mmols) of isopropylamine were still added and the mixture was heated overnight at reflux temperature. The mixture was avaporated to dryness under reduced pressure, then the residue was recrystallized from isopropanol. 4-(3-Isopropylamino-2-hydroxypropoxy)-3-methyl-2'-nitrobenzalinide was obtained Yield: 3.7 g (9.6 mmols; 80%) MP (°C.): 145–146.

(d) The preceding nitrated product (3.7 g; 9.6 mmols) was dissolved in 400 ml of absolute ethanol. 1.5 g of 5% palladium on carbon was added, then the solution was agitated in the presence of hydrogen under an initial pressure of 40 psi. After 1 hour, the catalyst is filtered off. The so obtained 2'-aminobenzanilide solution was added with 35 ml of concentrated hydrochloric acid and the mixture was heated for 4 hours at reflux temperature before being concentrated until a volume of about 100 ml. The mixture was then basified (pH 12) by addition of 2 N soda solution, then filtered. The so obtained benzimidazole was purified by recrystallization from ethyl acetate.

Yield: 2.4 g (7.2 mmols; 75%). MP (°C.): 155–156

| Elementary analysis | C | H | N |
| --- | --- | --- | --- |
| % calculated | 70.8 | 7.4 | 12.4 |
| % found | 70.6 | 7.5 | 12.3 |

EXAMPLE 5

2-[4-(3-isopropylamino-2-hydroxypropoxy)phenyl]-5(6)-methylbenzimidazole (hydrochloride).

In an apparatus allowing to work under pressure, 350 ml of ethanol, 3.7 g (8.5 mmols) of 1-benzyl-2-[4-(3-isopropylamino-2-hydroxypropoxy)phenyl]-5-methylbenzimidazole, 30 ml of 22% ethanolic hydrochloric acid, 0.5 gr of 5% palladium on carbon, then hydrogen were successively added at an initial pressure of 100 psi. The reaction was heated overnight at 45° C. The catalyst was then filtered off and the filtrate was evaporated to dryness under reduced pressure. The residue was taken up in 35 ml of water before adding 8.5 ml of 2 N aqueous soda slowly and with agitation. The solid was filtered and dried, then recrystallized from an ethyl acetate/isopropanol mixture 2/1. Monohydrochloride was obtained by adding the resulting product (2.3 g) to a mixture of 23 ml of anhydrous ether and 1.13 ml of 22% ethanolic hydrochloric acid. It was recrystallized from isopropanol.

Yield: 2.3 g (6.1 mmols; 72%) MP (°C.): 223–225.

| Elementary analysis | C | H | N |
|---|---|---|---|
| % calculated | 63.9 | 7.0 | 11.2 |
| % found | 63.8 | 6.8 | 11.4 |

EXAMPLE 6

2-[4-(3-isopropylamino-2-hydroxypropoxy)phenyl]-benzimidazole (dihydrated glucuronate).

A solution of 4.9 g (15 mmols) of the product of Example 1 in 80 ml of methanol was slowly added to a solution of 3.2 g (16.5 mmols) of β-D-glucuronic acid in a mixture of 100 ml of methanol and 20 ml of water. The resulting solution was agitated at room temperature overnight, then evaporated to dryness under reduced pressure. The oily residue was added with 100 ml of acetonitrile. The strong agitation of the mixture caused apparition of a white solid which is abundantly washed with ether and dried.

Weight: 7.4 g (13 mmols; 89%) MP (°C.): 135 (dec).

| Elementary analysis | C | H | N |
|---|---|---|---|
| % calculated | 54.0 | 6.7 | 7.6 |
| % found | 53.8 | 6.4 | 7.3 |

Table I groups derivatives of preceding examples as well as other derivatives of the invention prepared according to the hereinabove described process.

TABLE I

Structure: benzimidazole (with $R_3$) — phenyl (with $R_2$) — $OCH_2CHOHCH_2NHR_1$

| No | $R_1$ | $R_2$ | $R_3$ | MP (°C.) (9) | Recrystallization solvent |
|---|---|---|---|---|---|
| 1 | $iC_3H_7$ | H | H | 193–194 | iPrOH |
| 2 | $nC_8H_{17}$ | H | H | 152–153 | AcOEt/EtOH |
| 3 | $CH_2CH_2$—O—Ph | H | H | 152–153 | AcOEt/EtOH |
| 4 | $tC_4H_9$ | H | H | 204–205 | EtOH |
| 5 | $CH_2CH_2$—Ph(OCH$_3$)$_2$ | H | H | 162,5–163 | iPrOH |
| 6 | $(CH_2)_4$ | H | H | 165–166 | iPrOH |
| 7 | CH(CH$_3$)—CH$_2$CH$_2$—Ph | H | H | 103–104 | iPrOH/cyclohexane |
| 8 | $iC_3H_7$ | H | H | 294 (dec) | MeOH (1) |
| 9 | $iC_3H_7$ | H | H | 276 (dec) | H$_2$O (2) |
| 10 | $iC_3H_7$ | H | H | 266 (dec). | H$_2$O/DMF (3) |
| 11 | $iC_3H_7$ | H | H | 135 (dec) | CH$_3$CN (4) |
| 12 | $iC_3H_7$ | H | H | 115 (dec) | EtOH/Et$_2$O (5) |
| 13 | CH(CH$_3$)CH$_2$CH$_2$—Ph(O-CH$_2$-O) | H | H | 128,5–129 | AcOEt |
| 14 | $iC_3H_7$ | H | 5(6)-CH$_3$ | 223–225 | iPrOH (6) |
| 15 | $iC_3H_7$ | H | 5,6-(CH$_3$)$_2$ | >300 | MeOH (7) |
| 16 | $iC_3H_7$ | H | 5(6)-Cl | >300 | EtOH (7) |
| 17 | $iC_3H_7$ | H | 4(7)-NO$_2$ | 265 (dec) | MeOH/EtOH (8) |
| 18 | NH—cycloC$_6$H$_{11}$ | H | H | 220–221 | EtOH |
| 19 | $iC_3H_7$ | H | 5(6)-OCH$_3$ | 165–166 | acetone |
| 20 | $iC_3H_7$ | 3'-CH$_3$ | H | 155–156 | AcOEt |
| 21 | $CH_2CH_2$—O—Ph—Cl | H | H | 207–208 | EtOH |
| 22 | $CH_2CH_2$—O—Ph—CH$_3$ | H | H | 175–176 | EtOH |
| 23 | $(CH_2)_4S$—Ph | H | H | 105–106 | EtOH |
| 24 | $iC_3H_7$ | H | 5(6)-NO$_2$ | 167–168 | Acetonitrile |
| 25 | $iC_3H_7$ | 3'-OCH$_3$ | H | 175–176 | Acetonitrile |
| 26 | $(CH_2)_2NHCOiC_3H_7$ | H | H | 108–109 | iPrOH/EtOH |
| 27 | $(CH_2)_2NHCOCH_2C_6H_5$ | H | H | 156–157 | iPrOH/EtOH |
| 28 | $iC_3H_7$ | H | 5,6-Cl$_2$ | 193–193,5 | Acetonitrile |
| 29 | $nC_{18}H_{37}$ | H | H | 285–286 | EtOH (7) |

TABLE I-continued

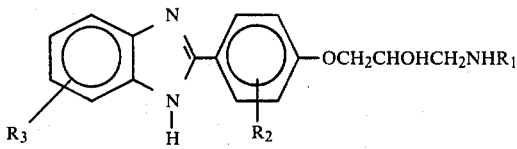

| No | R$_1$ | R$_2$ | R$_3$ | MP (°C.) (9) | Recrystallization solvent |
|----|-------|-------|-------|--------------|---------------------------|
| 30 | CH—C$_6$H$_{13}$<br>\|<br>CH$_3$ | H | H | (dec)<br>283–284<br>(dec) | EtOH (7) |
| 31 | (CH$_2$)$_2$NHCOcycloC$_5$H$_9$ | H | H | 184–185 | EtOH |
| 32 | iC$_3$H$_7$ | 3′-Br | H | 181–182 | iPrOH/AcOEt |

(1) 2HCl . 2H$_2$O
(2) H$_2$SO$_4$ . H$_2$O
(3) H$_3$PO$_4$
(4) glucuronate . 2H$_2$O
(5) hemiaspartate . H$_2$O
(6) HCl
(7) 2 HCl
(8) HCl . H$_2$O
(9) M (°C.): melting point Pharmacological and biochemical results for compounds of the invention are given in the following table II. In this table, numbers given in column 1 correspond to numbers of column 1 of Table I. Results given in this table have to be interpreted as follows.

drug is examined at 100, 30, 10 and possibly 3 mg/kg. The behaviour is studied 2, 4, 6 and 24 hours after treatment. The observation is extended when symptoms persist at this time. The mortalities are recorded during the 14 days following the treatment. None of the tested

TABLE II

BIOLOGICAL RESULTS.

| No | LD$_{50}$ | Antihypertensive activity | Chronotrope effect 10$^{-6}$M | β-lytic effect 10$^{-6}$M | β-lytic effect 10$^{-7}$M | Antispasmodic activity Hist. | Antispasmodic activity Ac. Chol. |
|----|-----|------------------|---|---|---|------|------|
| 1  | 2300  | ++++(174)       | 0  | 3 | 2 | 5.18 | 5.21 |
| 2  | >300  | 0               |    |   |   | 6.46 | 6.64 |
| 3  | >3000 | +++(50)         | 0  | 2 |   | 6.52 | 6.43 |
| 4  | 1425  | +++(192)        | 0  | 3 | 1 | 5.64 | 5.72 |
| 5  | >3000 | +++(34)         | 0  | 3 | 2 | 5.80 | 5.69 |
| 6  | >3000 | 0               | −1 | 0 |   | 6.89 | 7.12 |
| 7  | >3000 | +(18)           | 0  | 0 |   | 6.25 | 6.23 |
| 8  | >2248 | +++(66) at 10 mg | 0 | 4 |   | 4.65 | 4.95 |
| 9  | 2620  | +++(68) at 10 mg | 0 | 4 |   | 4.75 | 4.60 |
| 10 | 1960  | +++(61) at 10 mg | 0 | 4 |   | 4.31 | 4.95 |
| 11 | 1494  | +++(51) at 10 mg | 1 | 4 |   | 4.52 | 4.30 |
| 12 | 1950  | +++(160)        | 0  | 4 | 2 | 4.60 | 4.75 |
| 13 | >1000 | 0               | 0  | 2 |   | 6.46 | 6.15 |
| 14 | 1450  | ++++(83)        | 1  | 4 | 2 | 4.85 | 5.10 |
| 15 | 1450  | ++++(110)       | 0  | 3 | 1 | 5.45 | 5.38 |
| 16 | 1100  | ++++(90)        | 0  | 3 | 1 | 5.58 | 5.25 |
| 17 |       | ++++(89)        | 0  | 3 | 2 | 5.15 | 5.60 |
| 18 |       | +++(83)         | 0  | 1 |   | 5.45 | 5.21 |
| 19 |       | +++(59)         | 1  | 4 |   | 4.99 | 4.70 |
| 20 |       | 0               | 0  | 4 | 1 |      |      |
| 21 |       | 0               |    |   |   |      |      |
| 22 |       | 0               | 0  | 2 |   | 5,65 | 5,35 |
| 23 |       | 0               | 0  | 0 |   | 6,05 | 5,74 |
| 24 |       |                 | 0  | 3 | 2 | 5,50 | 5,45 |
| 25 |       |                 | 0  | 3 | 1 |      |      |
| 26 |       |                 | 0  | 4 | 3 |      |      |
| 27 |       |                 | 0  | 4 | 3 |      |      |

LD$_{50}$ were determined according to the Lichtfield and Wilcoxon method (J. Pharmacol. Exp. Ther. 96, 99, 1949) and expressed in mg/kg. The products were administered to mice orally.

The effect of the behaviour was studied when using a method deriving from that of S. Irwin (Gordon Res. Conf. on Medicinal Chem., 133, 1959). The substances in suspension in a 1% tragacanth gum mucilage were administered orally by means of an intragastric probe to groups of 5 male mice (Charles River CD$_1$ strain, fasted from 18 hours). If the available amount of substance allows it, the doses are 3000, 1000 and 300 mg/kg. In the case of this latter dose being active, the effect of the products has induced an abnormal behaviour in mouse.

The antihypertensive activity was tested by oral administration to unanesthetized spontaneously hypertensive rats, the systolic arterial pressure of which is measured at the level of the median coccygeal artery by the plethysmographic method (J. Roba, G. Lambelin, A. F. De Schaepdryver, Arch. int. Pharmacodyn. 200, 182, 1972). The arterial pressure is measured every 30 minutes, from 2 hours before to three hours after oral administration of products tested at 60 mg/kg or of a placebo (1% tragacanth gum mucilage). Only rats having a systolic pressure of 180 to 220 mm Hg are used. Two rats are used by product. The treatments are administered without the knowledge of the person making the measure.

The antihypertensive effects were recorded according to a score followed by an index. The scoring system is as follows:

0: reduction <10 mm Hg
+: reduction of 10 to 20 mm Hg
++: reduction of 20 to 30 mm Hg
+++: reduction of 30 to 50 mm Hg
++++: reduction >50 mm Hg.

The index is calculated by multiplying the systolic pressure difference (cmHg) measured every 30 minutes after the treatment, by a coefficient of 1 to 6 corresponding to times of 30 to 180 minutes.

In the test conditions, alpha-methyldopa was scored +++(47) at 100 mg/kg, reserpine +++(53) at 3 mg/kg and guanethidine +++(62) at 60 mg/kg.

The β-lytic effect was searched on the chronotropic response to noradrenaline of isolated guinea pig auricles. Auricles were incubated for 20 minutes in a Tyrode solution at 29° C. in the presence of the substance to be tested at the concentration of $10^{-6}$ M. A positive (+) or negative (−) chronotrope effect of the substance was noted using the following scores:

0 if the frequency modification was comprised between +6 and −6.
±1 if the frequency modification was comprised between ±7 and ±20.
±2 if the frequency modification was comprised between ±21 and ±40.
±3 if the frequency modification was higher than ±40.

Then, the chronotrope effect of cumulative increasing concentrations of noradrenaline was recorded. The $pD_2$ (−log CE50) value was calculated. A score of β-lytic activity of the substance was given as follows:

0 if $pD_2 \geq 6.81$
1 if $6.80 \geq pD_2 \geq 6.41$
2 if $6.40 \geq pD_2 \geq 6.01$
3 if $6.00 \geq pD_2 \geq 5.51$
4 if $pD_2 \leq 5.50$ If the score at concentration of $10^{-6}$ M was 3 or 4, the effect of the substance was examined at concentration of $10^{-7}$ M and a score was recorded according to the same procedure.

The antispasmodic activity of the studied substances was examined against guinea pig ileum contractions induced by histamine and acetylcholine.

These experiences allow to make it obvious an antihistaminic, anticholinergic or musculotrope activity. The response to the contracting agent (sub-maximum concentration) is obtained every 5 minutes before and after injection of increasing concentrations of tested products ($10^{-7}$ M to $10^{-4}$ M). The inhibition percentage under the influence of tested products is calculated and the theoretical concentration giving 50% of inhibition is graphically determined for each experience. These values are expressed in $-\log CI_{50}(M)$.

The peripheral vasodilator activity was measured on anesthetized dog at the level of femoral arterial circulation. To this end, the femoral artery the collaterals of which have been ligated is perfused at constant rate with blood taken from aorta. The perfusion pressure measured at the level of the femoral artery thus varies as a function of the resistance of the perfused area. The tested products and the corresponding solvents are directly injected at the dose of 30 μg/kg. The cardiac output being maintained constant, a vasodilation is thus measured by a decrease of the perfusion pressure. The latter is scored in comparison with the action of papaverine, considered as a reference and injected one time by group of 4 products. When interesting, the products are tested with other doses under the same conditions.

The vasodilator activity is appreciated as follows:

0: inactive <10 mm Hg of reduction
+: ⅓ of papaverine activity
++: ⅔ of papaverine activity
+++: activity equal to papaverine
++++: activity higher than papaverine Compounds 2,3,6,7 and 23 revealed as active in this test.

In general, compounds of the invention have a β-lytic activity. Compounds 1 and 5 were carefully studied in this respect.

The effect on $\beta_1$ cardiac receptors is measured by inhibition of the chronotropic response to noradrenaline of guinea pig auricles and of the inotrope response to isoproterenol of guinea pig left auricles which were electrically stimulated. The cardioselectivity is appreciated by measuring the antagonist effect at the level of $\beta_2$ receptors of the guinea pig trachea. To this end, a tracheal chain is contracted by a maximum concentration of histamine and inhibition of relaxation by isoproterenol is measured. The values calculated for cardioselectivity are obtained by considering the difference between $pA_2$ values of the chronotrope response and the relaxation on the one hand (1st column) and of the inotrope response and relaxation on the other hand (2nd column). For these various experiences, $pA_2$ is calculated according to the Van Rossum method (Arch. Inern. Pharmacodyn., 143, 299–330, 1963).

The results are given in table III where numbers of compounds correspond to numbers of compounds of Table I.

TABLE III

| | β-lytic activity. | | | |
|---|---|---|---|---|
| | $pA_2$ | | | |
| | Auricles | | | Cardio- |
| Compounds | chronotrope response | inotrope response | Trachea relaxation | selectivity. |
| 1 | 7.87 | 7.45 | 4.54 | 1.73 |
| 5 | 7.67 | 7.40 | <4.00 | >1.91 |
| Propanolol | 8.40 | 7.98 | 8.39 | 1 |
| Metroprolol | 8.09 | — | 6.28 | 1.28 |
| Atenolol | 7.35 | 6.89 | 5.64 | 1.30 |

The difference of $pA_2$ observed on auricles and on trachea indicates an important cardioselectivity of compounds 1 and 5 of the invention. It appears from this study that compound 1 is 2140 times more active on β cardiac receptors than on $\beta_2$ tracheal receptors. Compound 5 is more than 5600 times more active on $\beta_1$ receptors than on $\beta_2$ receptors. Metopropol and atenolol are 65 and 50 times respectively more active, while propanolol has on the contrary the same activity on both types of receptors, namely it is not cardioselective.

Compounds 1 and 5 are thus active β-agents on β cardiac receptors, their cardioselectivity being much higher than that of metopropol and atenolol.

Cardioselectivity of compound 1 was also demonstrated in vivo on anesthetised dog. When injected by i.v. way at the dose of 30 μg/kg, it blocks stimulation of cardiac receptors without affecting that of peripheral $\beta_2$ receptors.

The β-lytic activity of compound 1 was demonstrated in vigile rat after administration of 10 mg/kg orally (antoganism of tachycardia caused by isoprotenenol, 0.1 mg/kg transcutaneously).

Finally, some compounds of the invention inhibit agglutination of platelets in blood plasma. The measure of platelet agglutination inhibition was made according to the turbidimetric method of G. V. R. Born and M. J. Cross (J. Physiol., 168, 178, 1973). The plasma rich in platelets was preincubated for 4 minutes before addition of the inducing agent, namely Thrombofax. The variations of turbidity were recorded for a period of 10 minutes with a "Chronolog" agglutinometer. The inhibition of the maximum amplitude of agglutination was measured. In this test, compounds 1 and 2 revealed as being active.

For administration of the new compounds of the invention, the daily dose will be 10 mg to 2 g orally and 0.1 mg to 100 mg parenterally.

The products of the invention may be used as various galenic forms. Following examples are not limitative and relate to galenic formulations containing an active product of the invention designated by letter A and selected from the following group:

2-[4-(3-isopropylamino)-2-hydroxypropoxy]phenylbenzimidazole.
2-{4-[3-(2-phenoxyethylamino)-2-hydroxypropoxy]phenyl}benzimidazole.
2-{4-[3-[2-(3,4-dimethoxyphenyl)ethylamino]-2-hydroxypropoxy]phenyl}benzimidazole.
2-[4-(3-t-butylamino-2-hydroxypropoxy)phenyl]benzimidazole.
2-[4-(3-n-octylamino-2-hydroxypropoxy)phenyl]benzimidazole.
2-[4-(3-n-octadecylamino-2-hydroxypropoxy)phenyl]benzimidazole.
2-{4-[3-(2-octylamino)-2-hydroxypropoxy]phenyl}benzimidazole.
2-{4-[3-(2-phenylacetamidoethyl)amino-2-hydroxypropoxy]phenyl}benzimidazole.
2-{4-[3-(2-isobutyramidoethyl)amino-2-hydroxypropoxy]phenyl}benzimidazole.
2-{4-[3-(2-cyclopentylamidoethyl)amino-2-hydroxypropoxy]phenyl}benzimidazole.
2-[4-(3-isopropylamino-2-hydroxypropoxy)-3-bromophenyl]benzimidazole.
2-[4-(3-isopropylamino-2-hydroxypropoxy)-3-methoxyphenyl]benzimidazole.
2-[4-(3-isopropylamino-2-hydroxypropoxy)-2,6-dimethylphenyl]benzimidazole.
2-[4-(3-isopropylamino-2-hydroxypropoxy)-phenyl]-5(6)nitrobenzimidazole.

| Tablets. | |
|---|---|
| A | 200 mg |
| Soluble starch | 20 mg |
| Corn starch | 125 mg |
| microcrystalline cellulose | 45 mg |
| silicium oxide | 6 mg |
| magnesium stearate | 4 mg |
| A | 50 mg |
| mannitol | 123 mg |
| hydroxypropylmethylcellulose | 7 mg |
| talc | 5 mg |
| microcrystalline cellulose | 60 mg |
| hydrogenated castor oil | 5 mg |
| Gelatin capsules. | |
| A | 10 mg |
| Corn starch | 175 mg |
| polyvinylpyrrolidone | 10 mg |
| magnesium trisilicate | 5 mg |
| A | 100 mg |
| lactose | 116 mg |
| microcrystalline cellulose | 75 mg |
| silicium oxide | 3 mg |
| magnesium stearate | 6 mg |
| Suppositories. | |
| A | 250 mg |
| butylhydroxyanisole | 6 mg |
| semi-synthetical glycerides | 2900 mg |
| A | 100 mg |
| ascorbic acid | 20 mg |
| polyethylene glcyol | 2080 mg |
| Drinkable solutes. | |
| monohydrochloride of compound A equivalent to 20 mg of base | |
| saccharose | 600 mg |
| nipagine | 1 mg |
| aromatizing agent | 10 mg |
| sweetening agent | 20 mg |
| demineralised water | ad 1 ml |
| monohydrochloride of compound A equivalent to 100 mg of base | |
| propylene glycol | 400 mg |
| glycerine | 200 mg |
| ethyl alcohol | 50 mg |
| aromatizing agent | 15 mg |
| sweetening agent | 15 mg |
| demineralized water | ad 1 ml |
| Injectables. | |
| monohydrochloride of compound A equivalent to 2 mg of base | |
| water for injectables | ad 1 ml |
| monohydrochloride of compound A equivalent to 25 mg of base | |
| ethyl alcohol | 50 mg |
| propylene glycol | 200 mg |
| water for injectables | ad 1 ml |

We claim:

1. A benzimidazole derivative of the formula:

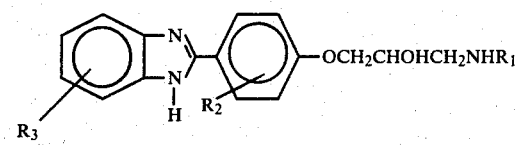

wherein:
$R_1$ is a:
C$_1$–C$_{18}$ straight or branched alkyl,
C$_3$–C$_8$ cycloalkyl,
C$_1$–C$_5$ straight or branched alkyl substituted by one or two phenyl, phenoxy, phenylthio, phenylsulfinyl groups, a
C$_1$–C$_4$ straight or branched alkyl, C$_1$–C$_4$ straight or branched alkoxy, methylenedioxy or halogen-substituted phenyl, phenoxy, phenylthio or phenylsulfinyl group,
C$_1$–C$_5$ straight or branched alkyl substituted by an optionally phenyl- or phenoxy substituted C$_1$–C$_6$ straight or branched alkylcarboxamido group, or a C$_1$–C$_5$ straight or branched alkyl substituted by a C$_3$—C$_8$ cycloalkylcarboxamido group;
$R_2$ is:
hydrogen,
one or two C$_1$–C$_4$ straight or branched alkyl groups,
one or two C$_1$–C$_4$ straight or branched alkoxy groups,
one or two halogen atoms;

$R_3$ is:
  hydrogen,
  one or two $C_1$–$C_4$ straight or branched alkyl groups,
  one or two $C_1$–$C_4$ straight or branched alkoxy groups,
  one or two halogen or nitro groups, and the esters derived from aliphatic carboxylic acids having up to 20 carbon atoms or from aromatic carboxylic acids comprising up to 10 carbon atoms, or the acid addition salts thereof with a non-toxic pharmaceutically acceptable acid.

2. The compound as claimed in claim 1 wherein:
$R_1$ is a $C_3$–$C_{12}$ alkyl, a $C_5$ or $C_6$ cycloalkyl or a $C_2$–$C_5$ alkyl substituted by
a phenyl, phenoxy, phenylthio or phenylsulfinyl group
a phenyl, phenoxy, phenylthio or phenylsulfinyl substituted by one or two methyl or methoxy groups, a methylenedioxy group or one or two halogen atoms,
a $C_1$–$C_4$ alkylcarboxamido group optionally substituted with a phenyl or phenoxy group,
a $C_5$–$C_6$ cycloalkylcarboxamido group each of $R_2$ and $R_3$ are one or two methyl or methoxy radicals, or $R_2$ and $R_3$ are both hydrogen.

3. The compound as claimed in claim 2 wherein $R_1$ is a $C_3$–$C_8$ alkyl, a $C_2$–$C_4$ alkyl substituted with phenyl, phenoxy, phenylthio, phenylsulfinyl or a phenyl, phenoxy, phenylthio, phenylsulfinyl substituted with one or two methyl, methoxy, methylenedioxy groups or one or two halogen atoms.

4. The compound as claimed in claim 1 or 2 wherein $R_1$ is a $C_6$–$C_{10}$ alkyl.

5. The compound as claimed in claim 1 or 2 wherein $R_1$ is a $C_3$ or $C_4$ alkyl.

6. The compound as claimed in claims 1 or 2 wherein $R_1$ is an alkyl substituted by
a phenyl, phenoxy, phenylthio group or a phenyl, phenoxy, phenylthio group substituted by one or two methyl or methoxy groups or a methylenedioxy group.

7. The compound as claimed in claim 1 wherein $R_1$ is an isopropyl, t-butyl, 2-phenoxyethyl, (1-methyl-3-phenyl) propyl, (1-methyl-4-phenyl)butyl, 4-phenyl-butyl or 2-(3,4-dimethoxyphenyl) ethyl group.

8. The compound as claimed in claim 1, 2 or 3 wherein halogen is fluorine, chlorine or bromine.

9. A compound as claimed in claim 1 selected from the group consisting of:
  2-[4-(3-isopropylamino-2-hydroxypropoxy)phenyl]-benzimidazole,
  2-[4-(3-t-butylamino-2-hydroxypropoxy)phenyl]benzimidazole,
  2-[4-(3-n-octylamino-2-hydroxypropoxy)phenyl]benzimidazole,
  2-4-[3[2-(3,4-dimethoxyphenylethyl)amino]-2-hydroxypropoxy]phenyl]benzimidazole,
  2-4-[3-(2-phenoxyethylamino)-2-hydroxypropoxy)-phenyl]benzimidazole,
  2-[4-(3-n-octadecylamino-2-hydroxypropoxy)phenyl]-benzimidazole,
  2-4-[3-(2-octylamino)-2-hydroxypropoxy]phenyl)benzimidazole,
  2-4l -[3-(2-phenylacetamidoethyl)amino-2-hydroxypropoxy]phenylbenzimidazole,
  2-4-[3-(2-isobutyramidoethyl)amino-2-hydroxypropoxy]phenylbenzimidazole,
  2-4-[3-(2-cyclopentylamidoethyl)amino-2-hydroxypropoxy]phenylbenzimidazole,
  2-[4-(3-isopropylamino-2-hydroxypropoxy)-3-bromophenyl]benzimidazole,
  2-[4-(3-isopropylamino-2-hydroxypropoxy)-3-methoxyphenyl]benzimidazole,
  2-[4-(3-isopropylamino-2-hydroxypropoxy)-2,6-dimethylphenyl]benzimidazole, and
  2-[4-(3-isopropylamino-2-hydroxypropoxy)-phenyl]-5(6)nitrobenzimidazole.

10. An antihypertensive composition containing as the active ingredient thereof an antihypertensive amount of a compound of claim 1 together with a pharmaceutically acceptable carrier or diluent.

11. A method of treating hypertension comprising administering to a subject in need of same an effective amount of a compound of claim 1.

12. The method as claimed in claim 1 wherein the amount is from 10 mg to 2 g orally administered.

13. The method as claimed in claim 1 wherein the amount is from 0.1 mg to 100 mg administered intravenously.

* * * * *